United States Patent
Gripon et al.

(10) Patent No.: US 7,892,754 B2
(45) Date of Patent: Feb. 22, 2011

(54) HEPATITIS B VIRUS PRE-S1 DERIVED SYNTHETIC POLYPEPTIDES AND USES THEREOF

(75) Inventors: Philippe Gripon, Rennes (FR); Stephan Urban, Neustadt-Allemagne (DE)

(73) Assignees: Institut National de la Sante Et de la Recherche Medicale (INSERM), Paris (FR); Stephen Urban, Neustadt-Allemagne (FR)

( * ) Notice: Subject to any disclaimer, the term of this patent is extended or adjusted under 35 U.S.C. 154(b) by 485 days.

(21) Appl. No.: 11/641,066

(22) Filed: Dec. 19, 2006

(65) Prior Publication Data

US 2007/0116721 A1 May 24, 2007

Related U.S. Application Data

(63) Continuation of application No. 10/484,923, filed as application No. PCT/IB02/02915 on Jul. 26, 2002, now abandoned.

(30) Foreign Application Priority Data

Jul. 27, 2001 (EP) .................................. 01402048

(51) Int. Cl.
*G01N 33/53* (2006.01)
*G01N 33/567* (2006.01)
*C12Q 1/70* (2006.01)
*A61K 39/00* (2006.01)
*A61K 39/29* (2006.01)

(52) U.S. Cl. ........................... 435/7.1; 435/5; 435/7.21; 424/184.1; 424/189.1

(58) Field of Classification Search ...................... None
See application file for complete search history.

(56) References Cited

U.S. PATENT DOCUMENTS 5,158,769 A * 10/1992 Neurath et al. ........... 424/189.1

OTHER PUBLICATIONS

Kramvis A, Kew MC. "Relationship of genotypes of hepatitis B virus to mutations, disease progression and response to antiviral therapy." J Viral Hepat. Sep. 2005;12(5):456-64.*
Gripon P, et al. "Efficient inhibition of hepatitis B virus infection by acylated peptides derived from the large viral surface protein." J Virol. Feb. 2005;79(3):1613-22.*
Keller, MA, "Passive immunity in prevention and treatment of infectious disease." Clin Microbiol Rev. Oct. 2000;13(4):602-14.*
Engelke et al. "Characterization of a hepatitis B and hepatitis delta virus receptor binding site." Hepatplogy, Apr. 2006;43(4):750-60.*
Kidd-Ljunggren K, et al. "Generic variability in hepatitis B viruses." J Gen Virol. Jun. 2002;83(Pt 6):1267-80. Review.*
Neurath AR et al. "Identification and chemical synthesis of a host cell receptor binding site on hepatitis B virus" Cell, 46:429-436, 1986.*

* cited by examiner

*Primary Examiner*—Bo Peng
(74) *Attorney, Agent, or Firm*—B. Aaron Schulman; Terry L. Wright; Stites & Harbison PLLC (57) ABSTRACT

The invention relates to a group of synthetic polypeptides, derived from the pre-S1 region of HBV, that efficiently interfere with early steps of an HBV infection. The peptides of the invention can be used in diagnostics for the detection of antigens and/or antibodies.

5 Claims, 5 Drawing Sheets

SEQUENCE LISTING

```
<160> NUMBER OF SEQ ID NOS: 18

<210> SEQ ID NO 1
<211> LENGTH: 78
<212> TYPE: PRT
<213> ORGANISM: Human hepatitis virus B

<400> SEQUENCE: 1

Met Gly Gln Asn Leu Ser Thr Ser Asn Pro Leu Gly Phe Phe Pro Asp
 1               5                  10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro
65                  70                  75

<210> SEQ ID NO 2
<211> LENGTH: 47
<212> TYPE: PRT
<213> ORGANISM: Human hepatitis virus B

<400> SEQUENCE: 2

Gly Gln Asn Leu Ser Thr Ser Asn Pro Leu Gly Phe Phe Pro Asp His
 1               5                  10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 3
<211> LENGTH: 30
```

```
<212> TYPE: PRT
<213> ORGANISM: Human hepatitis virus B

<400> SEQUENCE: 3

Ala Gly Ala Phe Gly Leu Gly Phe Thr Pro Pro His Gly Gly Leu Leu
 1               5                  10                  15

Gly Trp Ser Pro Gln Ala Gln Gly Ile Leu Gln Thr Leu Pro
            20                  25                  30

<210> SEQ ID NO 4
<211> LENGTH: 77
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 4

Gly Gln Asn Leu Ser Thr Ser Asn Pro Leu Gly Phe Phe Pro Asp His
 1               5                  10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly Ala
        35                  40                  45

Gly Ala Phe Gly Leu Gly Phe Thr Pro Pro His Gly Gly Leu Leu Gly
    50                  55                  60

Trp Ser Pro Gln Ala Gln Gly Ile Leu Gln Thr Leu Pro
65                  70                  75

<210> SEQ ID NO 5
<211> LENGTH: 67
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 5

Gly Gln Asn Leu Ser Thr Ser Asn Pro Leu Gly Phe Phe Pro Asp His
 1               5                  10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly Ala
        35                  40                  45

Gly Ala Phe Gly Leu Gly Phe Thr Pro Pro His Gly Gly Leu Leu Gly
    50                  55                  60

Trp Ser Pro
65

<210> SEQ ID NO 6
<211> LENGTH: 48
<212> TYPE: PRT
<213> ORGANISM: Human hepatitis virus B

<400> SEQUENCE: 6

Met Gly Gln Asn Leu Ser Thr Ser Asn Pro Leu Gly Phe Phe Pro Asp
 1               5                  10                  15

His Gln Leu Asp Pro Ala Phe Arg Ala Asn Thr Ala Asn Pro Asp Trp
            20                  25                  30
```

```
Asp Phe Asn Pro Asn Lys Asp Thr Trp Pro Asp Ala Asn Lys Val Gly
        35                  40                  45

<210> SEQ ID NO 7
<211> LENGTH: 47
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 7

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 8
<211> LENGTH: 37
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 8

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys
        35

<210> SEQ ID NO 9
<211> LENGTH: 28
<212> TYPE: PRT
<213> ORGANISM: Human hepatitis virus B

<400> SEQUENCE: 9

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala
            20                  25

<210> SEQ ID NO 10
<211> LENGTH: 27
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 10

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala
            20                  25

<210> SEQ ID NO 11
```

-continued

```
<211> LENGTH: 17
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 11

Gly Gln Asn Leu Ser Thr Ser Asn Pro Leu Gly Phe Phe Pro Asp His
 1               5                  10                  15

Gln

<210> SEQ ID NO 12
<211> LENGTH: 7
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 12

Gly Gln Asn Leu Ser Thr Ser
 1               5

<210> SEQ ID NO 13
<211> LENGTH: 48
<212> TYPE: PRT
<213> ORGANISM: Woolly monkey hepatitis B virus

<400> SEQUENCE: 13

Met Gly Leu Asn Gln Ser Thr Phe Asn Pro Leu Gly Phe Phe Pro Ser
 1               5                  10                  15

His Gln Leu Asp Pro Leu Phe Lys Ala Asn Ala Gly Ser Ala Asp Trp
             20                  25                  30

Asp Lys Asn Pro Asn Lys Asp Pro Trp Pro Gln Ala His Asp Thr Ala
         35                  40                  45

<210> SEQ ID NO 14
<211> LENGTH: 47
<212> TYPE: PRT
<213> ORGANISM: Woolly monkey hepatitis B virus
<220> FEATURE:
<221> NAME/KEY: LIPID
<222> LOCATION: (1)
<223> OTHER INFORMATION: MYRISTATE

<400> SEQUENCE: 14

Gly Leu Asn Gln Ser Thr Phe Asn Pro Leu Gly Phe Phe Pro Ser His
 1               5                  10                  15

Gln Leu Asp Pro Leu Phe Lys Ala Asn Ala Gly Ser Ala Asp Trp Asp
             20                  25                  30

Lys Asn Pro Asn Lys Asp Pro Trp Pro Gln Ala His Asp Thr Ala
         35                  40                  45

<210> SEQ ID NO 15
<211> LENGTH: 41
<212> TYPE: PRT
<213> ORGANISM: Duck hepatitis B virus

<400> SEQUENCE: 15

Met Gly Gln His Pro Ala Lys Ser Met Asp Val Arg Arg Ile Glu Gly
 1               5                  10                  15
```

-continued

```
Gly Glu Ile Leu Leu Asn Gln Leu Ala Gly Arg Met Ile Pro Lys Gly
            20                  25                  30

Thr Leu Thr Trp Ser Gly Lys Phe Pro
        35                  40

<210> SEQ ID NO 16
<211> LENGTH: 40
<212> TYPE: PRT
<213> ORGANISM: Duck hepatitis B virus
<220> FEATURE:
<221> NAME/KEY: LIPID
<222> LOCATION: (1)
<223> OTHER INFORMATION: MYRISTATE

<400> SEQUENCE: 16

Gly Gln His Pro Ala Lys Ser Met Asp Val Arg Arg Ile Glu Gly Gly
1               5                   10                  15

Glu Ile Leu Leu Asn Gln Leu Ala Gly Arg Met Ile Pro Lys Gly Thr
            20                  25                  30

Leu Thr Trp Ser Gly Lys Phe Pro
        35                  40

<210> SEQ ID NO 17
<211> LENGTH: 30
<212> TYPE: PRT
<213> ORGANISM: Human hepatitis virus B

<400> SEQUENCE: 17

Leu Asp Pro Ala Phe Arg Ala Asn Thr Ala Asn Pro Asp Trp
                5                   10

Asp Phe Asn Pro Asn Lys Asp Thr Trp Pro Asp Ala Asn Lys Val Gly
15                  20                  25                  30

<210> SEQ ID NO 18
<211> LENGTH: 30
<212> TYPE: PRT
<213> ORGANISM: Human hepatitis virus B
<220> FEATURE:
<221> NAME/KEY: LIPID
<222> LOCATION: (1)
<223> OTHER INFORMATION: MYRISTATE

<400> SEQUENCE: 18

Leu Asp Pro Ala Phe Arg Ala Asn Thr Ala Asn Pro Asp Trp
                5                   10

Asp Phe Asn Pro Asn Lys Asp Thr Trp Pro Asp Ala Asn Lys Val Gly
15                  20                  25                  30
```

HEPATITIS B VIRUS PRE-S1 DERIVED SYNTHETIC POLYPEPTIDES AND USES THEREOF

This application is a continuation application of abandoned U.S. Application Ser. No. 10/484,923, having a filing date of Jul. 13, 2008, the date of completion of all requirements under 35 U.S.C. 371, and which is a National Stage application of PCT/IB02/02915, filed Jul. 26, 2002.

The present invention relates to new polypeptides and derivatives thereof that block Hepatitis B infection at an early step.

Hepadnaviruses are a group of small-enveloped partially double stranded DNA viruses, which have been found in mammals and birds. The human hepatitis B virus (HBV), representing the prototype of this group, causes acute and chronic hepatitis in man. Infections with the HBV represent a severe health problem, leading to an estimated one million death per year.

The intracellular replication cycle of hepadnaviruses, in particular transcription of the viral DNA, packaging and reverse transcription of genomic RNA and establishment of an intracellular pool of covalently closed circular HBV-DNA has been elucidated in some detail (Nassal et al, 1993; Nassal et al, 1996). However, until now the lack of an HBV-infectable cell line and the restricted availability of primary human hepatocytes for in vitro infection studies relentlessly prevented progress in the understanding of the early steps of the HBV-infection. Accordingly a variety of HBV-receptor candidates have been proposed on the bases of binding studies (reviewed by DeMeyer et al, 1997), but none of them could be convincingly demonstrated to be involved in the entry process.

However, more progress has been made recently in determining the sequence requirements for infection in the envelope proteins of duck and human hepatitis B virus (Urban et al., 1998, LeSeyec et al., 1998, LeSeyec et al., 1999).

The virus shell of HBV contains the large (L-), the middle (M-) and the small (S-) viral envelope proteins. Avian hepadnaviruses comprise only L- and S-protein. The surface proteins of all hepadnaviruses are encoded in single open reading frames of the viral DNA such that the L-protein contains the complete S-domain which serves as an anchor in the ER membrane-derived lipid bilayer. In the case of HBV, L- and M-proteins differ from S-protein in an hydrophilic N-terminal extension of 163 to 174 amino acids, termed pre-S. This pre-S extension is further divided into a pre-S2 (55 amino acids) and a pre-S1 (108 amino acids in subtype ayw) domain, towards the amino terminus. Depending on the HBV subtype, the pre-S1 domain shows some sequence variation and in case of subtype adr carries an insertion of additional 11 amino acids.

The analysis of the infectivity of pseudotyped HBVs carrying mutations in the exterior pre-S part of the L-protein has shown that the infection depends on an extended sequence within the pre-S1 domain of the HBV L-protein (Le Seyec, 1999). In contrast, major parts of the pre-S2 domain turned out to be dispensable for infectivity (Le Seyec et al, 1998). This indicates that the sequence between amino acids 3 and 77 of the pre-S1 domain is involved in the infection step.

Due to the availability of primary duck hepatocytes more progress has been achieved in the related duck hepatitis B virus model system. Using this system it was shown that *E. coli*-derived preS-polypeptides of the duck hepatitis B virus L-protein inhibit DHBV-infection of primary duck hepatocytes by interfering with receptor binding (Urban et al., 1998). It was further demonstrated that the DHBV-preS binding protein Carboxypeptidase D, initially identified by Kuroki et al., (1994) functions as a common receptor component for avian HBVs (Urban et al, 1998; Breiner et al, 1998; Urban et al, 2000).

In the case of HBV infection, a similar state of knowledge is still missing and there is yet no experimental evidence for peptide components that efficiently interfere with early steps of an HBV-infection.

The authors of the present invention have investigated whether recombinant, *E. coli* derived preS-polypeptides and chemically synthesized preS-peptides of HBV L-protein could interfere with a HBV-infection.

They have identified a group of synthetic peptides that exhibits at the same time an excellent direct inhibitory activity against HBV infection and makes it possible to elicit immune protection against HBV.

These polypeptides were designed from the sequence of the pre-S1 amino acids 1 to 78 (SEQ ID NO: 1) of the Hepatitis B virus subtype ayw. However, although these polypeptides are shorter than the pre-S1 region, they surprisingly show a better inhibitory activity than longer polypeptides that would mimic the entire pre-S1 region.

The isolated synthetic polypeptides, or variant thereof, of the present invention have an amino acid sequence of the formula:

$$X\text{-}Y\text{-}Z \qquad (I)$$

wherein:

X is an amino acid, for instance a methionine, or absent;

Y is the amino acid sequence 2 to 48 of pre-S1 region shown in SEQ ID NO: 2, or a N-terminally and/or C-terminally truncated form of this sequence, or variants thereof;

Z, linked to the —CO— group of the last residue of Y, is an amino acid sequence comprising 1 to 30 consecutive amino acids from the pre-S1 region shown in SEQ ID NO: 3, or absent;

said polypeptides being optionally chemically modified to bear a hydrophobic moiety.

Preferably, when Y is a C-terminally, and optionally N-terminally, truncated form of sequence SEQ ID NO: 2, or a variant thereof, Z is absent.

Preferably, the hydrophobic moiety corresponds to the acyl rest of a saturated or unsaturated fatty acid having at least 4 carbon atoms, preferably at least 6 carbon atoms, more preferably at least 8 carbon atoms, such as myristic acid, palmitic acid, stearic acid, oleate, linoleate, linolenate or arachidonate for instance, or the hydrophobic moiety corresponds to a cholesterol group or the like.

In a preferred embodiment, the polypeptides of the present invention are myristoylated. More preferably, the polypeptides comprise the entire amino acid sequence from 2 to 48 of SEQ ID NO: 1, amino acid 2 (glycine) carrying a myristyl group: Myr-GQNLSTSNPLGFFPDHQLDPAFRANTAN-PDWDFNPNKDTWPDANKVG (Myr 2-48, SEQ ID NO: 7).

In another embodiment, the polypeptide of the invention has the sequence SEQ ID NO: 4, SEQ ID NO: 5 or SEQ ID NO: 7.

The term "variant" refers to the homologous polynucleotidic sequences found in the different viral species, strains or subtypes of the hepadnavirus genus, such as HBV strain alpha1, HBV strain LSH (chimpanzee isolate), woodchuck HBV, Woolly Monkey HBV (WMHBV), or strains selected from the group consisting of the HBV subtypes AD, ADR, ADW, ADYW, AR and AYW.

Any analogs to the pre-S1 synthetic polypeptides are part of the present invention. Analogs involve amino acid deletions, amino acid substitutions such as conservative or non conservative replacement by other amino acids or by isosteres (modified amino acids that bear close structural and spatial similarity to protein amino acids), amino acid additions or isostere additions, as long as the sequences elicit 70% inhibition of human hepatocyte primary cultures HBV infection with a peptide concentration below 100 µM, preferably below 10 µM, and preferably below 1 µM.

Conservative amino acid substitutions typically relates to substitutions among amino acids of the same class. These classes include, for example, amino acids having uncharged polar side chains, such as asparagine, glutamine, serine, threonine and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Advantageously, peptides according to the invention are modified to resist proteolysis. This can be achieved for instance by substituting L-amino acids at exposed sites with their D-amino acid counterpart.

In another embodiment, the polypeptides of the invention can incorporate short peptidic or non peptidic linkers so as to design three-dimensionally constrained peptides (Root M. J. et al., 2001).

The polypeptides of this invention can be prepared by a variety of procedures readily known to those skilled in the art. Such procedures include more particularly the solid phase sequential and block synthesis (B. W. Erickson and R. B. Merrifield, 1976). The solid phase sequential procedure can be performed using established automated methods such as by use of an automated polypeptide synthesizer. In this procedure an α-amino protected amino acid is bound to a resin support. The resin support employed can be any suitable resin conventionally employed in the art for the solid phase preparation of polypeptides, preferably polystyrene which has been copolymerized with polyoxyethylen to provide sites for ester formation with the initially introduced o-amino protected amino acid. This optimized method, applied by the inventors, has been explicitly described by Gausepohl et al, 1989 and 1990.

The amino acids are introduced one by one. Each synthesis cycle corresponding to the introduction of one amino acid includes a deprotection step, successive washing steps, a coupling step with activation of the amino acid, and subsequent washing steps. Each of these steps is followed by a filtration.

The reactive agents for coupling are the classical reactive agents for polypeptide synthesis such as dicyclohexylcarbodiimide, hydroxybenzotriazole, benzotriazil-1-yl-oxytris (dimethylamino) phosphonium hexafluorophosphate, and diphenylphosphorylazide.

After synthesis of the polypeptide on the resin, the polypeptide is separated from the resin by a treatment with a strong acid such as trifluoroacetic acid in the presence of anisole, ethanedithiol or 2-methylindole. The compound is then purified by the classical techniques of purification, in particular by means of high pressure liquid chromatography (HPLC).

The polypeptides of the present invention may also be obtained by coupling polypeptide fragments that are selectively protected, this coupling being effected in a solution.

The polypeptide can further be produced by genetic engineering techniques. An eukaryotic expression system, such as the baculovirus system, is particularly suitable. According to this procedure proteins are expressed in insect cells infected with a recombinant baculovirus containing a nucleic acid sequence encoding a heterologous protein and regulating nucleic acid sequences, such as a promoter. Several cell-lines are available for infection with recombinant baculovirus, such as cell line SF-9, available from the American Type Culture Collection (CRL 1711).

The polypeptides of the present invention can be used to inhibit in vitro or in vivo hepatocyte infection by HBV through preventing binding and/or internalisation of HBV particles to hepatocytes.

Accordingly, the invention provides a method of in vitro inhibition of hepatocyte infection by HBV comprising using a polypeptide as described above.

Suitable hepatocytes include human primary hepatocytes or the hepatoma derived cell line called HepaRG (described in the patent application FR 0109044), which is also susceptible to HBV infection.

The invention further relates to a method for in vitro and/or in vivo identification of a hepatocyte receptor involved in the attachment and/or penetration of HBV and/or quantitation of the expression of said receptor that comprises using a peptide as described above.

In particular, said method comprises the steps consisting of:

- contacting a liver biopsy or a hepatocyte with a polypeptide of the invention under conditions and for a period of time sufficient to allow specific binding of said polypeptide to a receptor expressed at the surface of a hepatocyte;
- detecting binding of said polypeptide to a receptor; and
- identifying said receptor.

This can be achieved according to classical procedures well-known by the skilled in the art. For instance, this could involve radioactive, enzyme or fluorescent labelling of the polypeptides of the invention, and subsequent detection with an appropriate method. A number of fluorescent materials are known and can be utilized as labels. These include, for example, fluorescein, rhodamine, auramine, Texas Red. Enzyme labels consists in conjugation of an enzyme to a molecule of interest, e.g. a polypeptide, and can be detected by any of colorimetric, spectrophotometric, or fluorospectrophotometric techniques.

The present invention also relates to antibodies directed against a polypeptide according to the invention, or a fragment of said polypeptide. The antibodies of the present invention can be chimeric antibodies, humanized antibodies, or antigen binding fragments Fab, Fab', F(ab')2 and Fv. They can also be immunoconjugated or labelled antibodies.

Polyclonal antibodies can be obtained from serum of an animal immunized against a polypeptide of the invention, according to standard methods well-known by one skilled in the art. The specificity of the polyclonal serum can be further increased through immuno-affinity chromatography using polypeptides of the formula (I), or fragment thereof, immobilised on a solid phase. The antibody is contacted with the immobilised immunising polypeptide during a time sufficient to allow the formation of a complex antibody-immobilised polypeptide.

Monoclonal antibodies can be obtained according to the standard method of hybridoma culture (Kohler and Milstein, 1975).

Said antibodies are particularly useful for inhibiting in vitro or in vivo HBV infection of hepatocytes, or for ex vivo assessing the infectivity of HBV particles.

Accordingly, the invention provides a method for assessing ex vivo the infectivity of HBV particles comprising using an antibody according to the invention.

In another embodiment, the polypeptides or antibodies of the invention can be used as a drug. Such a drug can be particularly useful for blocking or preventing HBV infection.

Pharmaceutical compositions comprising, in a pharmaceutical acceptable carrier, either a polypeptide or an antibody according to the invention are within the scope of the invention.

Accordingly, the invention provides a therapeutical method for the prevention or the treatment of HBV infection that comprises administration of a peptide or antibody of the invention to a patient in need thereof.

The invention further relates to the use of a polypeptide or an antibody of the invention for the manufacture of a medicament intended for the in vivo inhibition of HBV infection. As used herein, the term "treatment" is intended for the improvement or the stabilisation of the condition of a patient. This include for instance prevention of HBV propagation to uninfected cells of an organism.

The invention further provides a therapeutical composition that comprises a polypeptide or antibody of the invention associated to a pharmaceutically acceptable carrier.

In another aspect, the invention relates to a method of vaccination against HBV infection that comprises administration of a peptide of the invention to a patient in need thereof.

Accordingly, the present invention includes a vaccinal composition comprising, in a pharmaceutically acceptable carrier, a polypeptide disclosed herein.

In the context of the present application, "vaccination" is intended for prophylactic or therapeutical vaccination. "Therapeutical vaccination" is meant for vaccination of a patient with HBV infection.

In further aspect, the invention provides a immunogenic composition comprising in a pharmaceutical acceptable support, a polypeptide disclosed herein.

Preferably, the peptide(s) of the vaccine method/composition or immunogenic composition is myristoylated. Myristoylation indeed makes it possible to enhance the immune response elicited toward the peptide antigen.

The polypeptides of the invention can be modified to have increased immunogenic properties. Such increased immunogenic properties refer for instance to increasing the range of antibodies elicited following immunization, or to allowing the production of antibodies capable of neutralizing infection by various viral strains.

In another embodiment, the polypeptides of the invention can be modified to decrease their immunogenic properties. Such polypeptides would be particularly useful in a therapeutical application to inhibit in vivo HBV infection while avoiding or limiting adverse effects.

A "pharmaceutically acceptable carrier" refers to any vehicle wherein the pharmaceutical or vaccine compositions according to the invention may be formulated. It includes a saline solution such as phosphate buffer saline. In general, a diluent or carrier is selected on the basis of the mode and route of administration, and standard pharmaceutical practice.

According to the invention, the term "patient" is meant for any human likely to be infected with HBV.

Polypeptides of the invention can be used for ex vivo diagnosis of HBV infection through detecting the interaction of said polypeptides with antibodies present in a biological sample and directed against a fragment of the pre-S1 region of HBV viral particles. The specific interaction of said polypeptides with endogenous antibodies can be detected by any suitable detection method readily known by the skilled in the art.

The invention thus provides a method for ex vivo diagnosis of HBV infection comprising the steps consisting of:
  contacting a biological sample with a polypeptide of the invention under conditions and for a period of time sufficient to allow formation of complexes between said polypeptide and an antibody present in a biological sample and directed against a fragment of the pre-S1 region of HBV viral particles;
  detecting said complexes, the presence of which is indicative of HBV infection.

The diagnosis method of the invention is useful as a predictive method of HBV infection development. Accordingly, repetitions at different points in time of the above ex vivo diagnosis method make it possible to reveal an increase or a decrease in the number of antibodies against a fragment of the pre-S1 region of HBV viral particles that are detected. An increase in the number of said antibodies usually indicates an improvement of the patient's condition. In particular, such a method allows assessment of a patient's response to a treatment.

Detection can be achieved through any means, e.g. radioactive, enzyme or fluorescent labelling of the polypeptides of the invention combined with appropriate means of detection, readily known by one skilled in the art.

The present invention is also directed to diagnostic methods relating to the detection antibodies to pre-S1 gene-encoded HBV antigens. Such antibodies can be detected ex vivo in a biological sample with the synthetic peptidic immunogens disclosed herein by both sandwich type immunoassays and competition type immunoassays, such as those immunoassays in which antigen in the sample competes with labelled immunogen for antibody.

Therefore, the invention further concerns a method for detecting a HBV infection comprising effecting quantitative immunoassays on a serum taken form a human to determine the amount of antibodies present therein, which are antibodies to an antigen coded by the pre-S1 region, employing the above-described HBV peptide immunogen and comparing the value with a known standard.

The invention also relates to a method for detecting the presence of HBV infection comprising effecting quantitative immunoassays on a serum taken form a human to determine the amount of antigens coded by the pre-S1 region, employing the above-described antibodies to the HBV peptide immunogen and comparing the value with a known standard.

Both peptides or antibodies according to the invention can similarly be used to determine the outcome of HBV infection by periodically carrying out an immunoassay on a biological sample from a patient so as to assess the amount of antibodies to an antigen coded by the pre-S1 region, or antigens coded by the pre-S1 region.

The invention will be further understood in view of the following examples and the annexed figures wherein.

EXAMPLE 1

Material and Methods for the Inhibition of HBV Infection with Pre-S1-HBV Synthetic Polypeptides a) Establishment of HBV-Infectable Cell Culture Fragments of normal adult human liver were obtained from patients undergoing hepatic resection for liver metastases (the fragments were taken at a distance from the metastasis in macroscopically normal liver). Access to this biopsy material was in agreement with French laws and satisfied the requirements of the French National Ethics Committee. Hepatocytes were isolated by the procedure of Guguen-Guillouzo and Guillouzo and cultured in H medium supplemented with 3.5× 10$^{-6}$ M hydrocortisone hemisuccinate, 2 mM L-glutamine, 50 mg of gentamicin per litre, 2% dimethyl sulfoxide, 5% adult human serum, and 5% FCS. Three days after seeding, the cells were infected.

Alternatively, for some experiments, instead of using primary cultures, we made use of a new hepatoma derived cell line, called HepaRG, which is also susceptible to HBV infection (patent application FR 0109044). Before the infection procedure cells were allowed to differentiate, allowing cells to gain an hepatocyte-like morphology (patent application FR 0109044). Cells were then infected.

b) HBV Infection of Cell Culture

As an infectious inoculum, a 50-fold concentrated culture medium of HepG2 clone 2.2.15 cells was used, because of an unlimited supply and a constant quality.

It was prepared as described previously. Differentiated cells were incubated with the concentrated infectious source, 10-fold diluted in culture medium supplemented with 5% PEG 8000 (Sigma), for 20 h at 37° C. as described previously (Gripon et al., 1988; Gripon et al., 1993). Control cultures were incubated with 5% PEG and 25% FCS diluted in phosphate-buffered saline (PBS) instead of the infectious source. At the end of the incubation, cells were washed three times with the culture medium and maintained in the presence of 2% DMSO and 5×10$^{-5}$ M hydrocortisone hemisuccinate and harvested at indicated times.

c) Polypeptide Competition Assays

Polypeptide competition assays were performed by pre-incubating cells with the analyzed polypeptide for 30 min, at 37° C., prior to the addition of the infectious source.

d) Inhibition of HBV Infection Assessment

HBsAg Assay

HBsAg was detected in the medium by an ELISA kit (Monolisa AgHBs plus) obtained from Bio-Rad Laboratories. Values are expressed in ng/ml of supernatant or percent of control (absence of peptide).

RNA Extraction and Analysis

Total cellular RNA was extracted by Total SV RNA kit (Promega, France), fractionated on a 1.5% agarose gel and analyzed by standard Northern blot procedure (Sambrook et al., 1989). Control of the RNA amount transferred onto filters was performed after methylene blue staining. Hybridization was performed with p$^{32}$ labeled HBV DNA.

EXAMPLE 2

Figure 1:
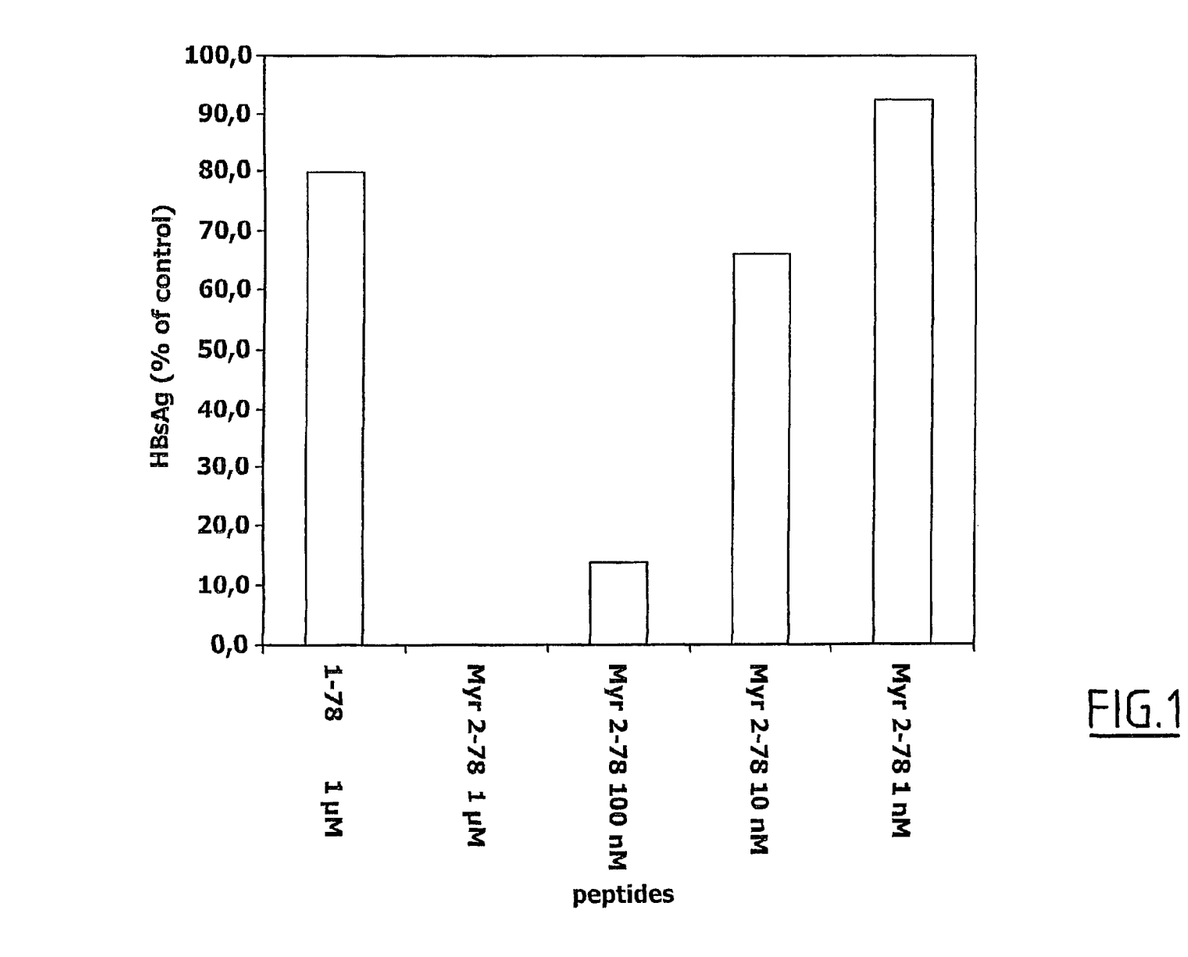
FIG. 1 is the comparison of HBV infectivity of human hepatocytes cultured in the presence of a myristoylated or non myristoylated peptide corresponding to a preS1 region domain (1-78). The infection efficiency was evaluated by measuring HBsAg in the supernatant of infected cells, 14 days post-infection. Values are expressed as a % of the control (no peptide).

Results of HBV Infection Inhibition with Pre-S1-HBV Synthetic Polypeptides a) Influence of the Myristoylation of pre-S1 Synthetic Peptides on HBV Infection Inhibition Mutagenesis experiments have previously shown that a part (amino acids (AA) 3-77) of the pre-S1 region was essential for HBV infectivity (Le Seyec et al., 1999). In addition we have also demonstrated that myristoylation of the AA 2, a glycine residue, associated with the removal of AA 1, a methionine residue, was also critical (Gripon et al., 1995). We have therefore postulated that a peptide comprising amino acids 2-77, with a myristoylated glycin, could interfere with the HBV infection process. To evaluate this hypothesis two peptides were synthesized: PreS 1-78 and Myr PreS 2-78. These peptides were then added prior and during the infection process of human hepatocyte cultures, the infection level was evaluated by measuring the HBsAg secretion of infected cells. FIG. 1 displays that although the non-myristoylated peptide has only a faint effect on HBV infectivity at 1 µM, the same amount of the myristoylated peptide did almost completely abolish it, lower doses were partly inhibitory. These results were confirmed by RNA analysis.

Other experiments conducted with higher peptide concentrations (up to 100 µM) indicate that myristoylation is not absolutely required for the inhibition of HBV infection but strongly enhances the activity of the peptides by a factor of about 100 fold.

b) Activity of C-terminally Truncated pre-S1 Synthetic Peptides

Figure 2:
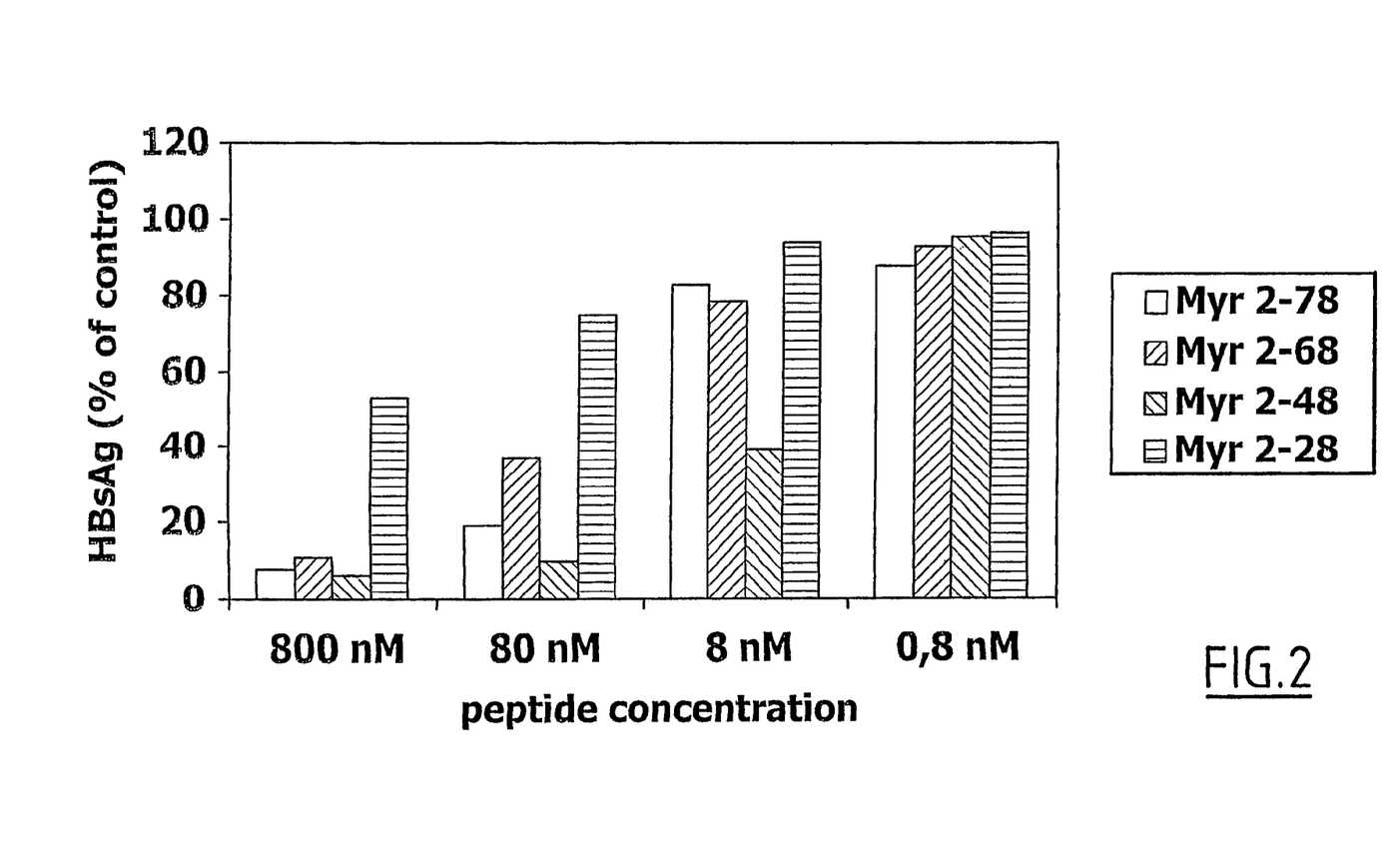
FIG. 2 illustrates the comparison of inhibitory activity of C-terminally truncated myristoylated peptides. Human hepatocytes were HBV infected in the presence of myristoylated or non-myristoylated peptides corresponding to parts of the Pre-S1 domain of the HBV L protein. The concentration of peptides ranged from 0.8 to 800 nM. Infection efficiency was evaluated by measuring HBsAg secretion 7 days after infection and expressed as a % of the positive control.

Human hepatocytes were HBV infected in the presence of myristoylated or non-myristoylated peptides corresponding to parts of the Pre-S1 domain of the HBV L protein. The concentration of peptides ranged from 0.8 to 800 nM. FIG. 2 shows the inhibition activity of myristoylated truncated peptides. Results obtained with non-myristoylated peptides are displayed in Table 1 (infra).

It appears that peptide Myr 2-48 shows the highest inhibitory activity. The larger peptides, Myr 2-68 and Myr 2-78, although very efficient at 800 nM are less active at lower doses. The smaller peptide Myr 2-28 is largely less active although a 50% inhibition is observed at 800 nM.

Figure 3:
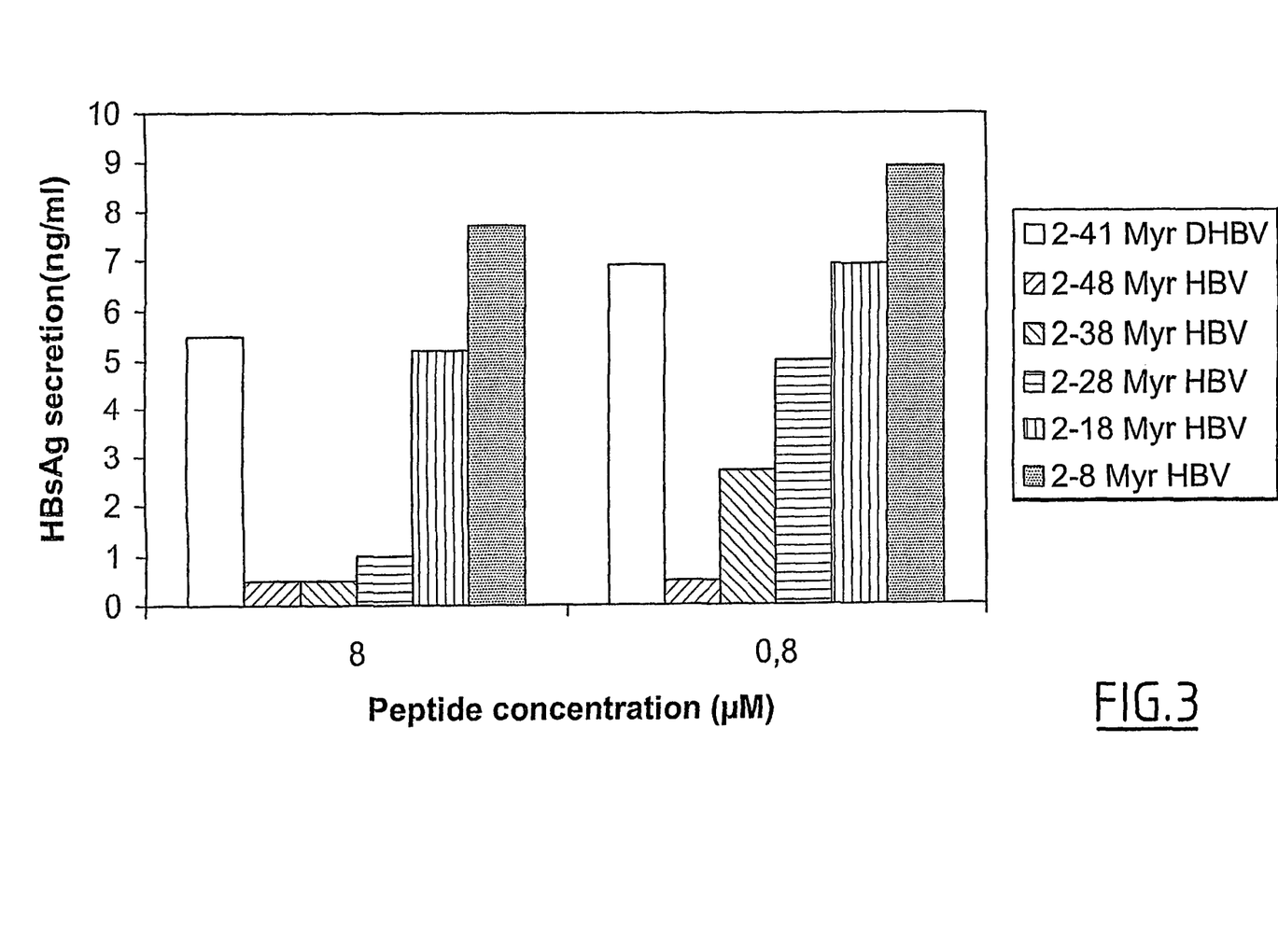
FIG. 3 is the comparison of the inhibitory activity of C-terminally truncated peptides shorter than Myr 2-48. The concentration of peptides ranged from 0.8 to 8 µM. Infection efficiency was evaluated by measuring HBsAg secretion 8 days after infection and expressed in ng/ml.

As some activity still persists for the peptide smaller than 2-48, in order to evaluate the contribution of the N-terminal amino acids, we have produced and evaluated a new set of short peptides. The results are shown on FIG. 3. From this figure it is obvious that Myr 2-38 and Myr 2-28 peptides still retain a significant inhibitory activity as they almost completely blocks HBV infection at 8 µM. By contrast the 2 shorter peptides are no longer active and the shorter one tends to increase HBV infectivity, for unknown reasons.

The effect of myristoylation and C-terminal truncation of pre-S1 peptides was also studied through RNA analysis. The results confirm that myristoylated truncated peptides displayed enhanced inhibitory activity as compared to the corresponding non myristoylated peptides, and that the highest inhibitory activity is obtained with Myr 2-48.

c) HBV Infection Inhibitory Activity of Pre-S1 Homologous Sequences

A recently discovered primate hepadnavirus, the Wolly Monkey Hepatitis B virus (WMHBV) has been shown very poorly infectious for Chimpanzee and for human hepatocyte primary cultures. The WMHBV pre-S 1-78 polypeptidic sequence shows 66% sequence identity to the original HBV derived peptide. We have investigated the inhibitory activity of a WMHBV derived Myr 2-48 peptide (SEQ ID NO: 14) towards HBV infection of human cells.

Figure 4:
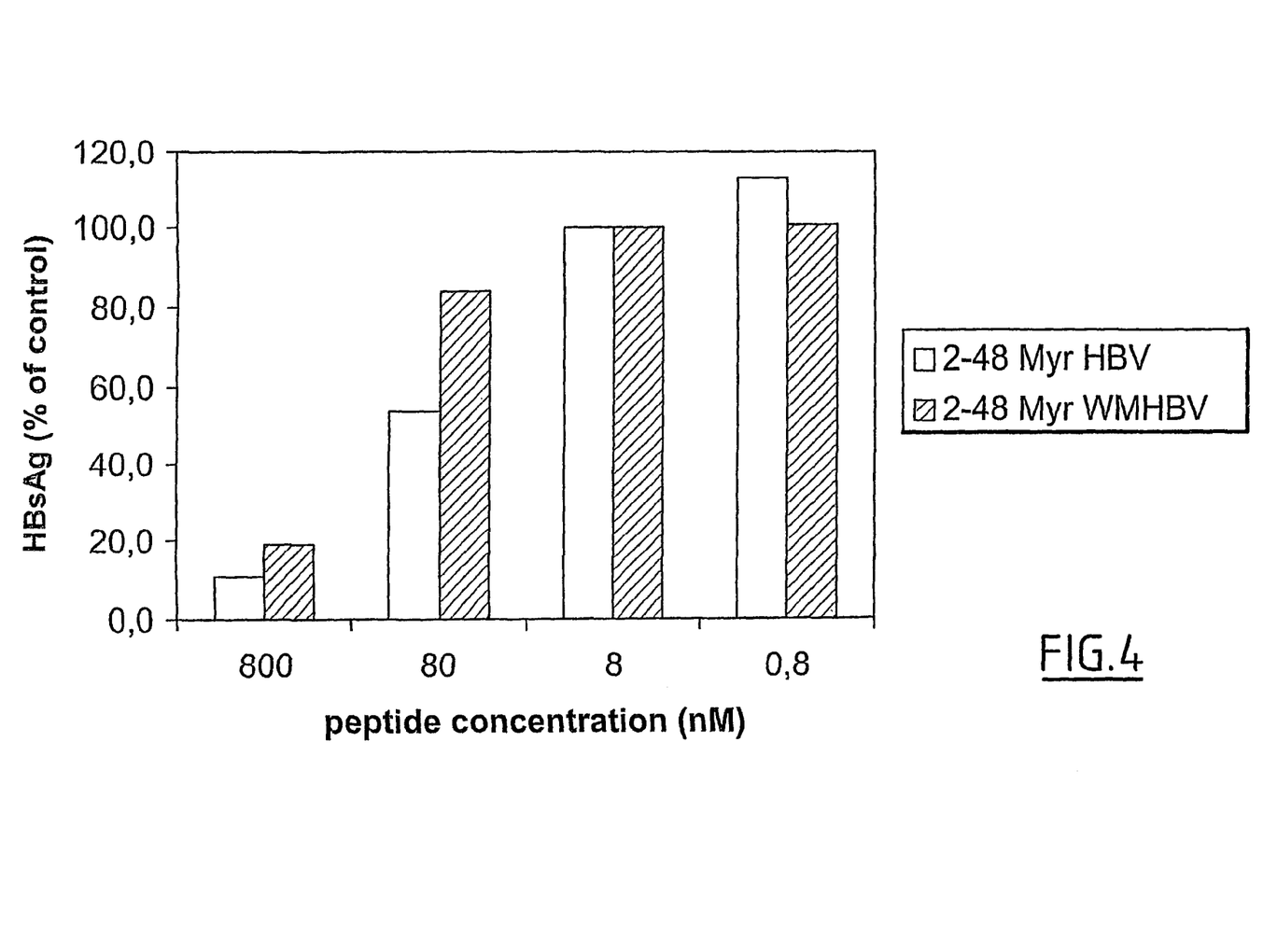
FIG. 4 illustrates the comparative inhibitory activity of WMHBV and HBV derived myristoylated 2-48 peptides. Infection of human primary human hepatocytes with HBV was performed in the presence of decreasing concentration of peptides. The supernatant of infected cells was collected at day 10 post-infection and analysed for the presence of HbsAg.

FIG. 4 illustrates the comparative inhibitory activity of WMHBV and HBV derived myristoylated 2-48 peptides (64% sequence identity). This experiment clearly shows that the WMHBV derived peptide is surprisingly nearly as efficient as the HBV derived peptide in inhibiting the HBV infection. This result is in contrast with the complete absence of activity of a DHBV derived peptide (PreS Myr 2-41 (SEQ ID NO: 16), see table 1) on HBV infection although this peptide is a strong inhibitor of DHBV infection.

Figure 5:
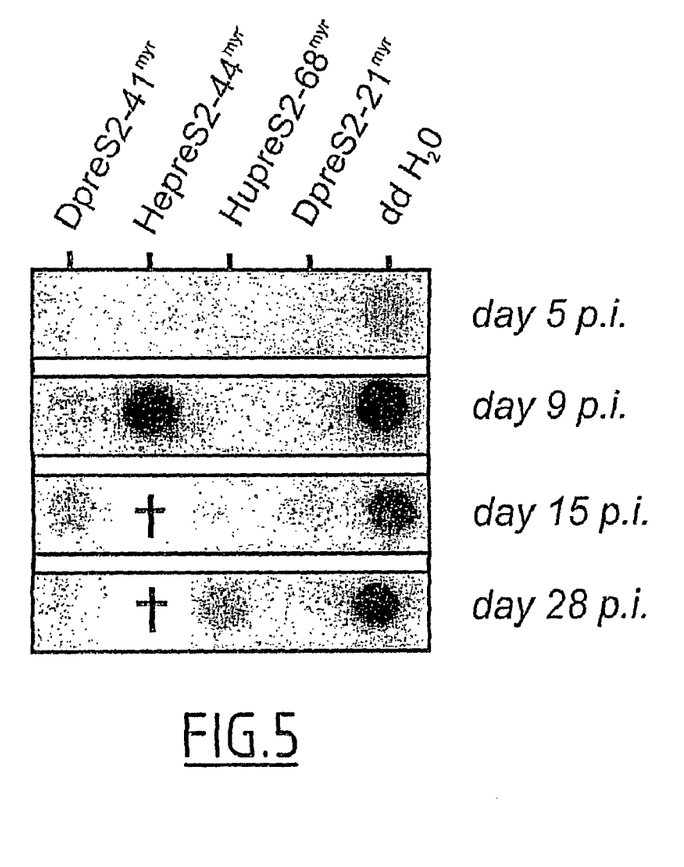
FIG. 5 is a Dot Blot analysis of duck HBV (DHBV) in the serum of ducks treated with duck preS Myr 2-41 (DpreS2-41$^{myr}$), heron preS Myr 2-44 (HepreS2-44$^{myr}$), human preS Myr 2-68 (HupreS2-68$^{myr}$), duck preS Myr 2-21 (DpreS2-21$^{myr}$) or ddH$_2$O, 5, 9, 15 and 28 days post-infection (p.i.) with DHBV.

From these results we can conclude that it is possible to efficiently inhibit the HBV infection. The tolerance of up to 46% variations in the peptide sequence suggests that it will be possible to inhibit the infection of HBV viruses of all genotypes with a single peptide.

reS2-44$^{myr}$), human preS Myr 2-68 (HupreS2-68$^{myr}$), duck preS Myr 2-21 (DpreS2-21$^{myr}$) or ddH$_2$O. The viremia of infected animals is assessed by Dot Blot analysis of viral DNA, 5, 9, 15 and 28 days post-infection. The results displayed in FIG. 5 show that viral DNA is detected in control animals treated with ddH$_2$O, indicated a successful infection of these animals. On the contrary, a transitory viremia can be observed at days 9 and 15 post-infection in ducks treated with either DpreS2-41$^{myr}$ or DpreS2-21$^{myr}$. At day 28, viral DNA is decreased or no longer detectable which suggests that the animals eliminated the virus. This analysis is further supported by the Western Blot analysis shown in FIG. 6 that shows the L protein of DHBV is not detected in the serum of ducks treated with either DpreS2-41$^{myr}$ or DpreS2-21$^{myr}$ 35 days post-infection.

Figure 6:
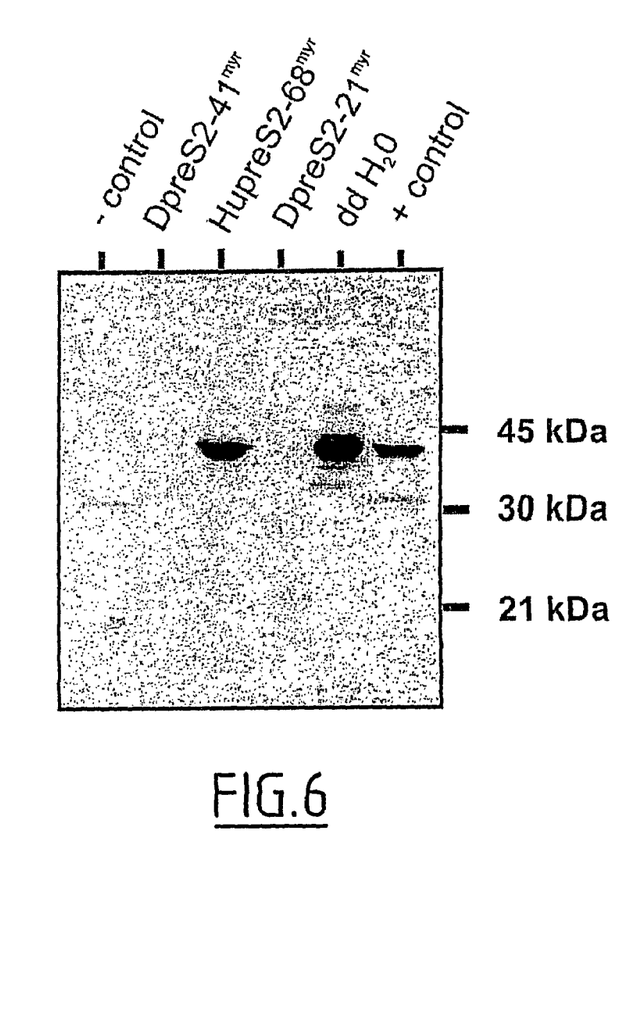
FIG. 6 is a Western Blot analysis of DHBV L protein in the serum of ducks 35 days post infection.

On the contrary, the human peptide HupreS2-68$^{myr}$ seems to delay but do not prevent infection of ducks with DHBV (FIGS. 5 and 6).

Since peptide DpreS2-21$^{myr}$ was shown to have no in vitro inhibitory activity towards DHBV infection of primary duck hepatocytes, the in vivo protection observed with this peptide would result from an indirect effect of the peptide, i.e. enhancement of the immune response through eliciting antibodies directed against DpreS2-21$^{myr}$.

This experiment illustrates that myristoylated synthetic peptides can confer protection against hepatitis B virus infection.

TABLE 1 summary of the results of the competition experiments.

| Non myristoylated polypeptides (100 µM) | HBV infectivity of human hepatocytes inhibition | Myristoylated polypeptides (1 µM) | HBV infectivity of human hepatocytes inhibition |
|---|---|---|---|
| HBV PreS 1-78 (SEQ ID NO: 1) | ND | HBV Myr PreS 2-78 (SEQ ID NO: 4) | ++++ |
| HBV PreS 1-68 (SEQ ID NO: 2) | ND | HBV Myr PreS 2-68 (SEQ ID NO: 5) | ++++ |
| HBV PreS 1-48 (SEQ ID NO: 6) | +++ | HBV Myr PreS 2-48 (SEQ ID NO: 7) | +++++ |
| HBV PreS 1-38 (SEQ ID NO: 3) | ND | HBV Myr PreS 2-38 (SEQ ID NO: 8) | +++ |
| HBV PreS 1-28 (SEQ ID NO: 9) | + | HBV Myr PreS 2-28 (SEQ ID NO: 10) | ++ |
| HBV PreS 1-18 (SEQ ID NO: –) | ND | HBV Myr PreS 2-18 (SEQ ID NO: 11) | – |
| HBV PreS 1-8 (SEQ ID NO: –) | ND | HBV Myr PreS 2-8 (SEQ ID NO: 12) | – |
| HBV PreS 19-48 (SEQ ID NO: 17) | – | HBV Myr PreS 19-48 (SEQ ID NO: 18) | – |
| WMHBV PreS 1-48 (SEQ ID NO: 13) | +++ | WMHBV Myr PreS 2-48 (SEQ ID NO: 14) | +++++ |
| DHBV PreS 1-41 (SEQ ID NO: 15) | – | DHBV Myr PreS 2-41 (SEQ ID NO: 16) | – |

ND: Not Determined

EXAMPLE 3

In Vivo DHBV Infection Inhibition with Pre-S-HBV Synthetic Polypeptides

Ducks are simultaneously injected with DHBV and duck preS Myr 2-41 (DpreS2-41$^{myr}$), heron preS Myr 2-44 (Hep-

REFERENCES

Breiner et al. (1998). Carboxypeptidase D (gp 180), a Golgi-resident protein, functions in the attachment and entry of avian hepatitis B viruses. J. Virol. 72:8098-8104;

DeMeyer et al. (1997). Organ and species specificity of hepatitis B virus (HBV) infection: a review of literature with a special reference to preferential attachment of HBV to human hepatocytes. *J. Viral Hepat.* 4, 145-153;

Gausepohl, H. et al. (1989). Int. J. Prot. Pept. Res. 34, 287-294.

Gausepohl, H. (1990). Peptidsynthesen an Polystyrol-Polyoxyethylen Pfropfcopolymeren im Vergleich zu anderen Trägern in der Festphasensynthese nach dem Durchflussprinzip, PhD thesis University of Tübingen.

Gripon, P., C. et al. (1988). Hepatitis B virus infection of adult human hepatocytes cultured in the presence of dimethyl sulfoxide. Journal of Virology. 62:4136-43.

Gripon, P., et al. (1993). Reproducible high level infection of cultured adult human hepatocytes by hepatitis B virus: effect of polyethylene glycol on adsorption and penetration. Virology. 192:534-40.

Guguen-Guillouzo et Guillouzo (1986). Methods for preparation of adult and fetal hepatocytes. p 1-12. In A. Guillouzo and C. Guguen-Guillouzo (ed.), Isolated and cultured hepatocytes. Les Editions INSERM Paris. John Libbey and Co, Ltd., London, United Kingdom.

Kuroki et al. (1994). A cell surface protein that binds avian hepatitis B virus particles. J. Virol. 68:2091-2096;

Le Seyec et al. (1998). Role of the preS2-domain of the large envelope protein in hepatitis B virus assembly and infectivity. *J. Virol.*, 72, 5573-5578.

Le Seyec et al. (1999). Infection process of the hepatitis B virus depends on the presence of a defined sequence in the pre-S1-domain. *J. Virol.*, 73, 2052-2057.

Nassal et al. (1993). Hepatitis B Virus replication. *Trends Microbiol.* 1, 221-228.

Nassal et al. (1996). H. Hepatitis B virus replication, an update. *J. Viral Hepatitis,* 3, 217-226.

Root, M. J. et. al. (2001). Science, 291:884-888.

Schlicht et al. (1987). Biochemical and immunological characterization of the duck hepatitis B virus envelope proteins. J. Virol. 61:2280-2285.

Urban et al. (1998). Avian hepatitis B virus infection is initiated by the interaction of a distinct preS-subdomain with the cellular receptor gp180. J Virol. 72:8089-8097.

Urban et al. (2000). Receptor recognition by a hepatitis B virus reveals a novel mode of high affinity virus-receptor interaction. EMBO J. 19 (6):1217-1227.

Urban et al. (1998). Avian hepatitis B virus infection is initiated by the interaction of a distinct preS-subdomain with the cellular receptor gp 180. J Virol. 72: 8089-8097.

Sambrook, J., E. F. Fritsh, and T. Maniatis. (1989). Molecular cloning, a laboratory manual. Cold Spring Harbor Laboratory Press, New York

---

The invention claimed is:

1. A method for inhibiting HBV infection of a cell in a subject, comprising administering to the subject a synthetic polypeptide of formula (I)

$$X-Y-Z \qquad (I)$$

wherein

X is an amino acid, or absent;

Y is the amino acid sequence consisting of amino acids 2 to 48 of the pre-S1 region of HBV large (L) envelope protein corresponding to SEQ ID NO: 2;

Z is either the amino acid sequence consisting of amino acids 49 to 78 of the pre-S1 region of HBV L envelope protein corresponding to SEQ ID NO: 3, linked to the —CO— group of the last residue of Y, or absent;

wherein the first amino acid of said polypeptide is myristoylated.

2. The method according to claim 1, wherein said pre-S1 sequence of HBV L envelope protein is selected from a group consisting of human HBV, chimpanzee HBV strain LSH, woodchuck HBV, and Woolly Monkey HBV.

3. The method according to claim 1, wherein the polypeptide has the amino acid sequence selected from a group consisting of SEQ ID NO: 4, SEQ ID NO: 5, SEQ ID NO: 7, SEQ ID NO: 8, SEQ ID NO: 13 and SEQ ID NO: 14.

4. The method of claim 2, wherein said human HBV is HBV strain alpha1.

5. The method of claim 2, wherein said human HBV is HBV subtypes ad, adr, adw, adv, w, ar or avw.

* * * * *